(12) United States Patent
Hoenes et al.

(10) Patent No.: US 8,015,685 B2
(45) Date of Patent: Sep. 13, 2011

(54) METHOD FOR PRODUCING A PUNCTURING AND MEASURING DEVICE

(75) Inventors: Joachim Hoenes, Zwingenberg (DE); Volker Zimmer, Dossenheim (DE)

(73) Assignee: Roche Diagnostics Operations, Inc., Indianaplis, IN (US)

( * ) Notice: Subject to any disclaimer, the term of this patent is extended or adjusted under 35 U.S.C. 154(b) by 1376 days.

(21) Appl. No.: 10/552,089

(22) PCT Filed: Apr. 1, 2004

(86) PCT No.: PCT/EP2004/003441
§ 371 (c)(1),
(2), (4) Date: Oct. 4, 2005

(87) PCT Pub. No.: WO2004/086970
PCT Pub. Date: Oct. 14, 2004

(65) Prior Publication Data
US 2006/0196031 A1    Sep. 7, 2006

(30) Foreign Application Priority Data

Apr. 4, 2003 (DE) .................. 103 15 544

(51) Int. Cl.
*B23P 11/00* (2006.01)
*A61B 17/32* (2006.01)
(52) U.S. Cl. ............ 29/432; 29/412; 29/414; 29/557; 606/181
(58) Field of Classification Search .......... 29/412, 29/414, 415, 416, 417, 432, 557; 606/181
See application file for complete search history.

(56) References Cited

U.S. PATENT DOCUMENTS

| | | | | |
|---|---|---|---|---|
| 2,801,633 A * | 8/1957 | Ehrlich | .......... | 606/181 |
| 2,896,628 A * | 7/1959 | Speelman | .......... | 606/181 |
| 3,046,987 A * | 7/1962 | Ehrlich | .......... | 606/181 |
| 3,517,670 A * | 6/1970 | Speelman | .......... | 606/181 |
| 3,665,672 A * | 5/1972 | Speelman | .......... | 53/435 |
| 3,822,461 A | 7/1974 | Malmstrom | | |
| 4,924,879 A | 5/1990 | O'Brien | | |
| 5,397,334 A * | 3/1995 | Schenk et al. | .......... | 606/182 |
| 5,582,184 A | 12/1996 | Erickson et al. | | |
| 5,591,139 A | 1/1997 | Lin et al. | | |
| 5,680,858 A | 10/1997 | Hansen et al. | | |
| 5,755,733 A * | 5/1998 | Morita | .......... | 606/182 |
| 5,801,057 A | 9/1998 | Smart et al. | | |
| 5,820,570 A | 10/1998 | Erickson et al. | | |
| 5,928,207 A | 7/1999 | Pisano et al. | | |
| 5,951,492 A | 9/1999 | Douglas et al. | | |
| 6,014,577 A | 1/2000 | Henning et al. | | |
| 6,102,927 A | 8/2000 | Wright | | |
| 7,169,117 B2 * | 1/2007 | Allen | .......... | 600/584 |

(Continued)

FOREIGN PATENT DOCUMENTS

CA    2 311 496    6/1999

(Continued)

*Primary Examiner* — Essama Omgba
(74) *Attorney, Agent, or Firm* — Baker & Daniels LLP

(57) ABSTRACT

The invention relates to a method for producing combined puncturing and measuring devices for detection of an analyte in liquid. The combined puncturing and measuring devices generally comprise a support and a detection element. Recesses which define the puncturing points are formed on one face of the band-shaped support material. A detection element is applied to the band-shaped support material. Individual puncturing/measuring disposable bodies are separated either singly or in groups from the band-shaped support material at a separating line.

22 Claims, 3 Drawing Sheets

U.S. PATENT DOCUMENTS

| | | | |
|---|---|---|---|
| 7,214,200 B2 * | 5/2007 | Raney et al. | 600/584 |
| 7,244,264 B2 * | 7/2007 | Roe et al. | 606/181 |
| 7,303,726 B2 * | 12/2007 | McAllister et al. | 422/68.1 |
| 7,322,996 B2 * | 1/2008 | Taylor et al. | 606/181 |
| 7,374,546 B2 * | 5/2008 | Roe et al. | 600/583 |
| 7,396,334 B2 * | 7/2008 | Kuhr et al. | 600/583 |
| 7,473,264 B2 * | 1/2009 | Allen | 606/181 |
| 7,479,118 B2 * | 1/2009 | Chan | 600/583 |
| 7,736,322 B2 * | 6/2010 | Roe et al. | 600/583 |
| 7,815,579 B2 * | 10/2010 | Roe | 600/584 |
| 2004/0193202 A1 * | 9/2004 | Allen | 606/181 |
| 2005/0021066 A1 * | 1/2005 | Kuhr et al. | 606/181 |
| 2005/0131440 A1 * | 6/2005 | Starnes | 606/181 |
| 2007/0191738 A1 * | 8/2007 | Raney et al. | 600/583 |
| 2007/0219462 A1 * | 9/2007 | Briggs et al. | 600/583 |
| 2009/0010802 A1 * | 1/2009 | Joseph et al. | 422/22 |
| 2009/0124933 A1 * | 5/2009 | Chan | 600/583 |
| 2009/0131964 A1 * | 5/2009 | Freeman et al. | 606/181 |

FOREIGN PATENT DOCUMENTS

| | | |
|---|---|---|
| DE | 198 46 250 | 4/1999 |
| DE | 197 53 847 | 6/1999 |
| EP | 0 199 484 | 10/1986 |
| EP | 0 861 670 A2 | 9/1998 |
| WO | WO 97/42888 | 11/1997 |

* cited by examiner

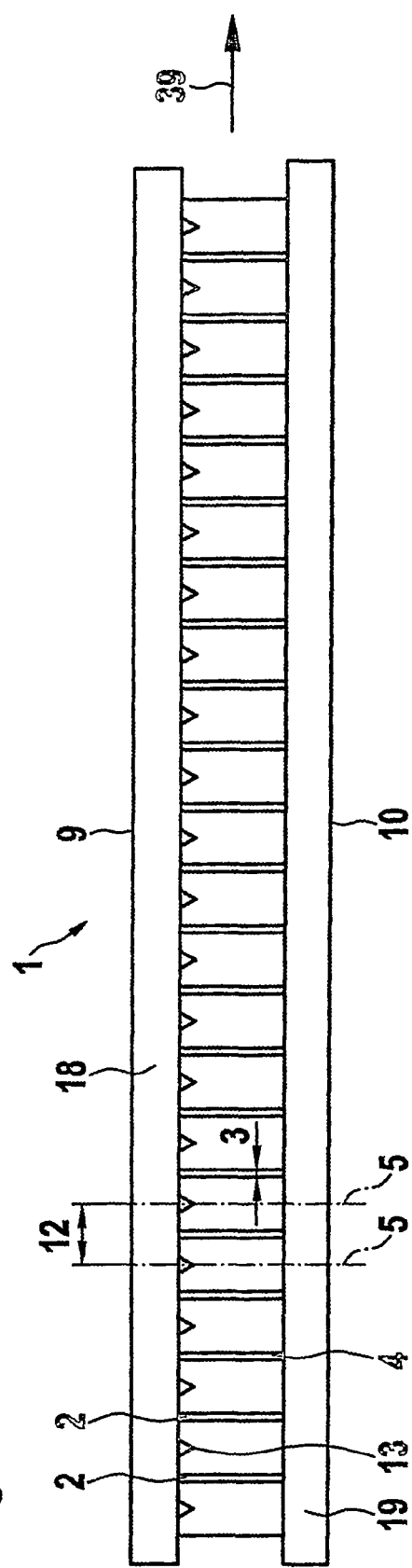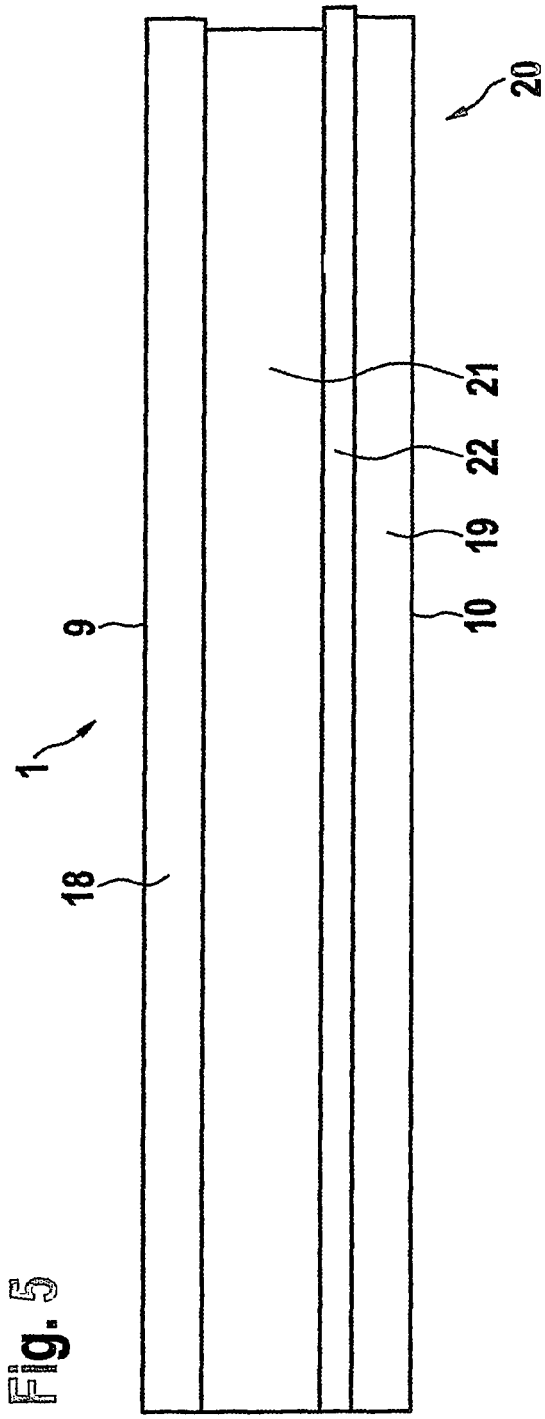

Fig. 6
Fig. 7
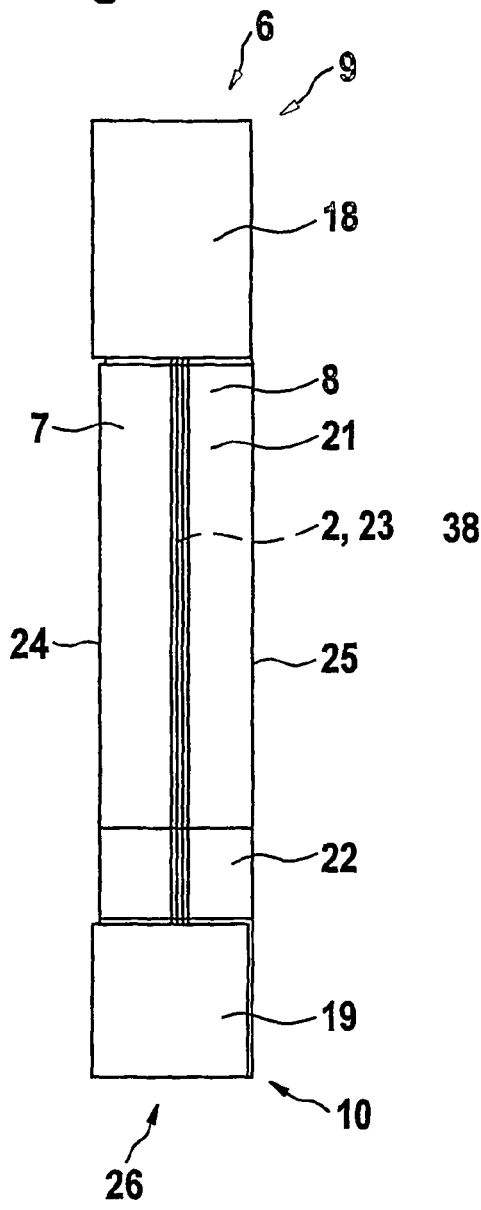
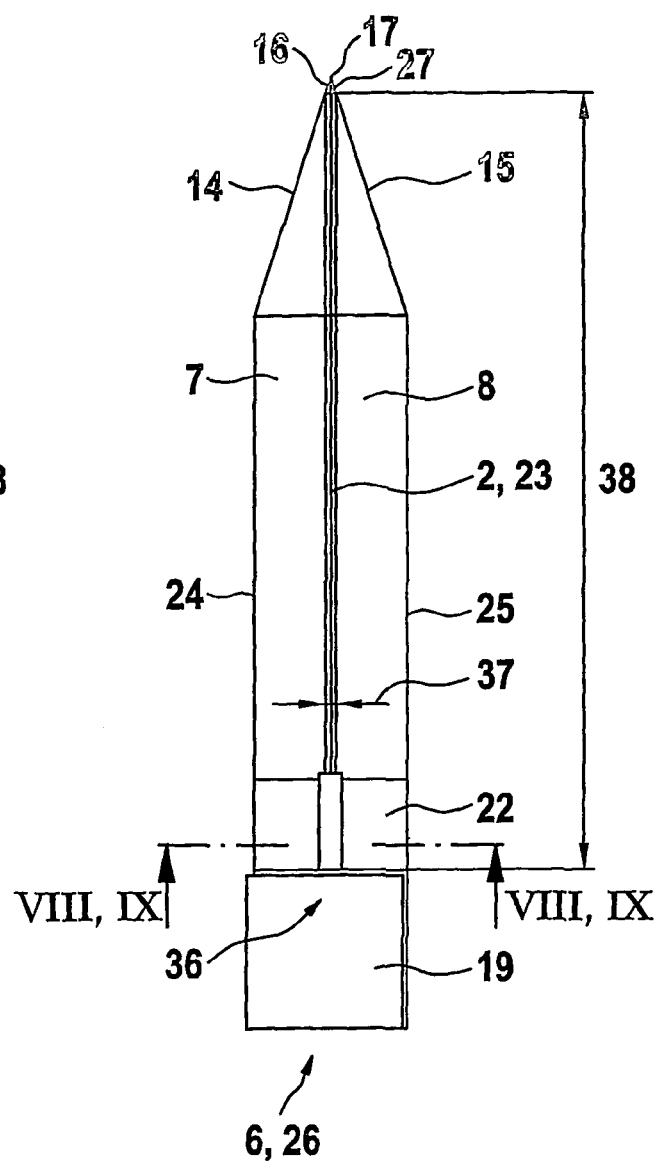
Fig. 8
Fig. 9
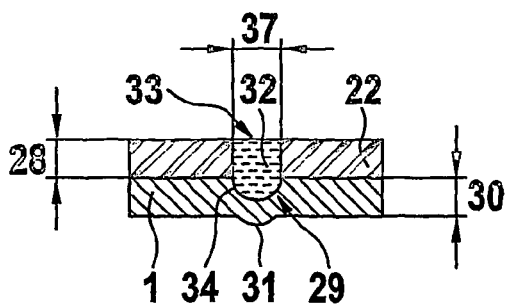
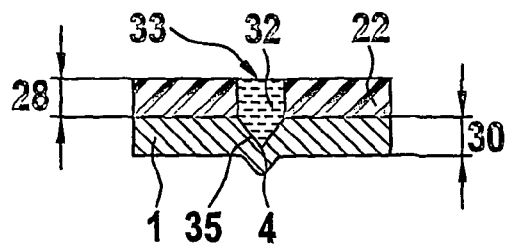

METHOD FOR PRODUCING A PUNCTURING AND MEASURING DEVICE

FIELD OF THE INVENTION

The present invention relates to a method for producing a puncturing and measuring device and to such a device, in particular for detection of analytes in body fluids.

BACKGROUND AND SUMMARY

Nowadays, disposable test strips or sensors are generally used for detection of analytes in body fluids from lancets and puncturing aids.

U.S. Pat. No. 3,822,461 discloses a disposable lancet for puncturing human skin in order to obtain a volume of blood. The lancet according to this solution is designed in such a way that a minimum amount of material is used to produce it and, consequently, production costs are kept low. The design of the disposable lancets allows a plurality of lancets to be punched out from one material strip, so as to guarantee economic production. According to the method disclosed in U.S. Pat. No. 3,822,461, in which individual lancets are obtained with a puncturing portion at one end of a metal strip, and with a shoulder formed there, the respective individual lancet is punched out from a material strip. The width of the material strip corresponds substantially to the length of the lancet. The lancets are punched out alternatingly from the strip, the tip of one lancet pointing in one direction, and the individual lancet to be punched out next to this one facing in the other direction. In each punching operation, individual lancets are obtained whose outer contour is defined by the punching tool. Each of the lancets punched out comprises an elongate depression which reaches from the handling end to the puncturing end of the lancet and stiffens the latter in such a way as to increase the stiffness and the security against bending of each lancet punched out from the continuous strip, so that the lancet does not buckle during use.

Furthermore, DE197 53 847 A1 discloses an analytical test element with a capillary channel. This analytical test element is used to determine an analyte in a liquid and comprises an inert support, a detection element, and a channel suitable for capillary liquid transport. This channel has a sample application opening at one end, and a vent opening at the other end. The channel suitable for capillary liquid transport is at least partially formed by the support and the detection element. The channel for capillary liquid transport reaches from the sample application opening at least as far as that edge of the detection element lying nearest the vent opening. A recess is situated in a surface forming the channel suitable for capillary liquid transport, at that edge of the test element forming the sample application opening. In this way, that edge of the test element forming the sample application opening is at least partially interrupted on one side, the surface located opposite the recess lying free. At least one of the faces forming the inner surface of the channel suitable for capillary liquid transport is made hydrophilic. This is done either by using a hydrophilic material or by coating a less hydrophilic material with a hydrophilic layer. A layer of oxidized aluminium, for example, is suitable for rendering it hydrophilic.

According to the solution known from DE 197 53 847 A1, a two-sided adhesive tape is affixed. This includes a cutout which is a few millimeters in width and several millimeters in length and by means of which the dimension of the capillary channel is defined. A detection film, specifically designed for the detection of glucose for example, is affixed to the adhesive tape. The detection film covers the central, notch-like cutout in the adhesive tape. A cover layer is affixed to the exposed area of the adhesive tape so that the cover layer and detection film lie directly on one another. The cover layer is a laminate of a relatively thick, stable plastic film and a thin hydrophilic $AluO_x$ layer. The hydrophilic layer has to extend into the gap between the cover layer and detection film. When the cover layer is fitted on the adhesive tape, it is necessary to arrange the protruding end of the thinner film, i.e. of the thin hydrophilic $AluO_x$ layer, between the detection element and the thicker film of the cover layer. In such a production method, errors can arise because of the large number of adhesion operations that have to be performed with great precision. Because of the method steps that have to be followed, this method is relatively time-consuming.

DE 101 42 232 A1 discloses an analytical aid with a lancet and a test element. The analytical aid includes a lancet having a lancet needle and a lancet body. The lancet needle is displaceable relative to the lancet body, the lancet body being made of an elastic material in the area of the tip of the lancet needle. This material is embedded into the tip of the lancet needle. An analytical test element is connected fixedly to the lancet body. Also disclosed is a lancet-containing analytical aid having a lancet which has a lancet needle and a lancet body. The lancet body is designed as a hollow body in the area of the tip of the lancet needle. The hollow body surrounds the tip of the lancet needle, said lancet needle being displaceable relative to the lancet body, and the hollow body being made at least partially of an elastic material, and an analytical test element which is connected fixedly to the lancet body.

An illustrated embodiment of the present invention provides a method by which puncturing and measuring devices may expediently be connected and may be produced in a substantially automated production process.

In one method step, a recess, preferably of triangular configuration, is produced on the band-shaped support material. In this way, a puncturing point is produced with which the human skin can be punctured. The edges delimiting the recess are ground and sharpened, in particular in the area of their point, so that a point suitable for puncturing the human skin is formed on one long side of the band-shaped support material. The side of the band-shaped support material, for which a thin metal film of 0.1 to 0.3 mm thickness can be used, is surrounded by a plastic material in order to protect against injuries and damage and to ensure sterility of the final product. A soft plastic strip, for example made of silicone, and surrounding the points, is preferably used for this purpose. That side of the band-shaped support material remote from the puncturing points is likewise provided with a strip of plastic material, in order to make handling easier, this strip of plastic material surrounding that side of the band-shaped support material is remote from the puncturing points. This strip, made of any desired plastic material, serves for better handling of the finished combination of lancet and test strip. At this stage in the production process, the band-shaped support material with the embedded lancet points, which are surrounded by soft plastic, for example silicone, can now be sterilized by β or γ irradiation.

By means of the method proposed according to the invention, individual puncturing/measuring disposable bodies can be produced in assembly line production while avoiding a separate movable lancet part. According to the proposed method, the lancet does not represent a separate individual part movable relative to the main body, as is known for example from DE 101 42 232 A1, but is instead a fixed component part thereof Thus, by means of the method proposed according to the invention, an assembly line production can be carried out which renders obsolete the separate transfer stage of joining together two components such as lancet and main body according to DE 101 42 232 A1.

The detection material is now applied to the band-shaped support material in which the puncturing points are formed and which is surrounded by a strip of silicone material at the side having the puncturing points, while the opposite side is provided with a strip of plastic material. The area between the soft plastic material covering the puncturing points and the plastic strip of the band-shaped support material facilitating handling is covered over with an affixed cover film which borders the detection element. The band-shaped support material is now completely covered over. At the side on which the ground and sharpened puncturing points are formed, the band-shaped support material is surrounded by a silicone strip, to which a cover film is adjoined. The cover film lies on a detection element which has been applied in strip form on the band-shaped support material and which in turn lies on the plastic material facilitating handling of the band-shaped support material. By means of the method proposed according to the invention, it is advantageously possible to ensure that the band-shaped support material, from which individual puncturing/measuring disposable bodies are separated, can be sterilized by β or γ irradiation prior to application of a detection element. After sterilization of the band-shaped support material is completed is the detection element applied, so that the function and mode of action of the detection element is not adversely affected by the sterilization of the band-shaped support material by β or γ irradiation, because it is not exposed to this irradiation, thanks to the fact that it is applied later to the band-shaped support material. The detection element can either be applied directly in the area of the sharpened puncturing points or can also be applied to depressions which have been incorporated in the band-shaped support material and which form a channel for capillary liquid transport. Both variations of the arrangement of the detection element are possible.

Individual puncturing/measuring disposable bodies are now separated at a separating edge which can be selected according to a division based on the width of the individual puncturing/measuring disposable bodies to be produced. The separation of the individual puncturing/measuring disposable bodies preferably takes place along a separating line which extends from the base of the recess symmetrically to the tip of the recess, which extends in each case between two grooves or notches. This separating line is an imagined virtual separating line and not actually formed in the band-shaped support material. Each of the individual puncturing/measuring disposable bodies formed in this way comprises a silicone material portion surrounding the puncturing point, a cover film covering the groove or notch, and a portion of a detection material adjoining these. Moreover, each of the individual puncturing/measuring disposable bodies produced in this way has, on the handling area, a portion of the plastic material. When the silicone strip portion is removed, the puncturing point is exposed. That portion of the individual puncturing/measuring disposable body surrounded by the plastic material is used for holding in a puncturing aid.

In a particularly advantageous manner, the puncturing and measuring devices can be produced from a continuous support material into which, according to one method step, depressions with a small width of approximately 0.25 mm have first been incorporated. An important feature of the application of the notches to the band-shaped support material is that the thin metal film preferably used as band-shaped support material, and of only a few tenths of a millimeter thick, is not pierced through, and instead form notches which, depending on the notching tool, can have a rounded notch base or a triangular notch base, for example. Other geometries of the base of the depressions are also possible.

By means of the individual puncturing/measuring disposable bodies produced in this way with a notch width or groove width of 0.25 mm and a notch length of 15 mm, it is preferably possible to collect approximately 100 nl of blood. The volume of the blood that can be taken up by the notch or groove and can be conveyed by capillary action to the detection element depends on the contour of the notch or groove. The measurement is performed using a suitable optics system which registers the wetted part of the detection field and evaluates its colour change.

The band-shaped support material used is preferably a thin metal film which as raw material is wound up in a coil, for example, and, during the production of the individual lancets, is removed from a store of the material at a certain speed of advance. Depending on the punching tool, whose geometry can be semicircular or triangular or of any other suitable form, the individual grooves or notches are applied on one side of the band-shaped support material.

The individual puncturing/measuring disposable bodies produced according to the production method set out here are characterized by low production costs per item, and it is also possible to ensure a uniform quality of the individual puncturing/measuring disposable bodies produced in this way.

BRIEF DESCRIPTION OF THE DRAWINGS

The invention is described in more detail below with reference to the drawing, in which:

FIG. 4 shows the puncturing points, covered by soft plastic strips, and a plastic material located opposite these and serving as a grip, FIG. 5 shows the application of a cover film and of a detection material between the silicone material and the plastic material on the top face of the band-shaped support material, FIG. 6 shows the plan view of an individual puncturing/measuring disposable body separated from the band-shaped support material and with covered puncturing point, FIG. 7 shows an individual puncturing/measuring disposable body with exposed puncturing point, FIG. 8 shows a cross section through the area of the individual puncturing/measuring disposable body, covered by the detection field, according to cross section line VIII-VIII, and FIG. 9 shows a cross section through the individual puncturing/measuring disposable body according to FIG. 7, according to cross section line IX-IX, the groove or notch having a triangular base.

DETAILED DESCRIPTION OF THE DRAWINGS

Figure 1:
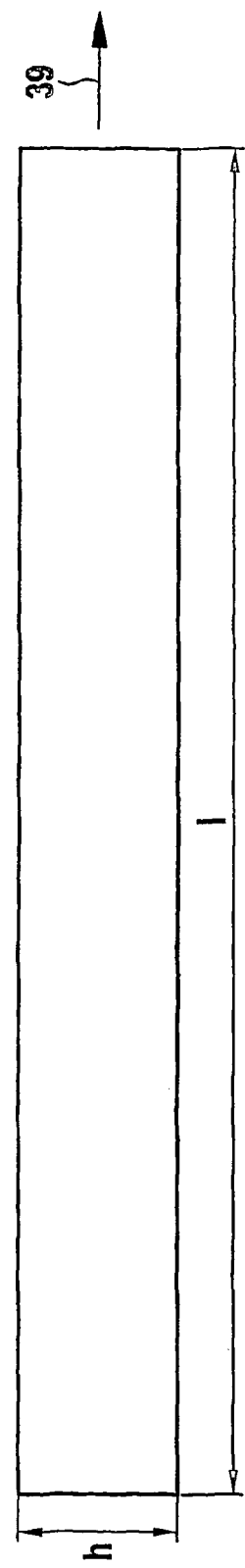
FIG. 1 shows the plan view of a band-shaped support material used as raw material.

FIG. 1 shows a band-shaped support material serving as an inert support body.

A band-shaped support material 1, which is preferably designed as a thin metal film with a thickness of between 0.1 and 0.3 mm, has a height h, and a length designated by 1. The band-shaped support material 1 configured as a thin metal film can be received on a winding reel and is unwound continuously from a store of material during the production of individual lancets. The height h of the band-shaped support material 1 is chosen such that it corresponds at least to the later overall height of an individual puncturing/measuring disposable body 6 to be produced (cf. FIGS. 6 and 7).

Figure 2:
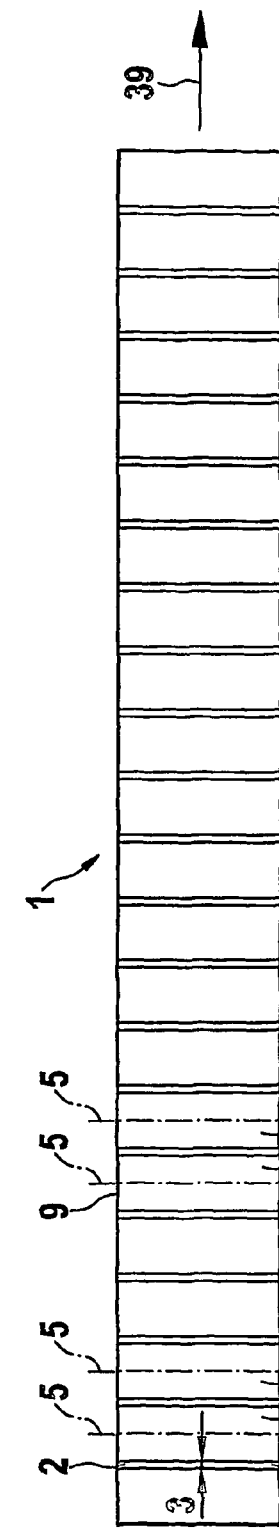
FIG. 2 shows the plan view of the band-shaped support material with depressions in the form of grooves or notches arranged in a selectable division.

The view according to FIG. 2 shows that depressions 2 can be embossed in the band-shaped support material 1 conveyed continuously in direction of advance 39. Depending on the geometry of the tool embossing the depressions 2 in the band-shaped support material 1, the depressions obtained are groove-shaped or notch-shaped and have a depression width 3. Depending on the geometry of the punch tool, a base 4 of the depression can be made round or triangular. In order to ensure that liquid is transported by capillary action through the depression 2 introduced into the band-shaped support material 1, other geometries of the punch tool or embossing tool can also be used. The depressions 2 embossed in the band-shaped support material 1 extend continuously from a first face 9 to a second face 10 of the band-shaped support material 1. Depending on the geometry of individual puncturing/measuring disposable bodies 6 which are to be separated from the band-shaped support material 1 in a subsequent method step, virtual separating lines 5 are provided which each extend between two depressions 2 embossed from the first face 9 and to the second face 10 of the band-shaped support material 1. The individual puncturing/measuring disposable body 6 which is later obtained, and which is separated from the band-shaped support material 1 along the separating lines 5 shown in FIG. 2, comprises a first lancet part 7 and a second lancet part 8 between which the depression 2 extends, preferably in the axis of symmetry of the individual puncturing/measuring disposable body 6.

Figure 3:
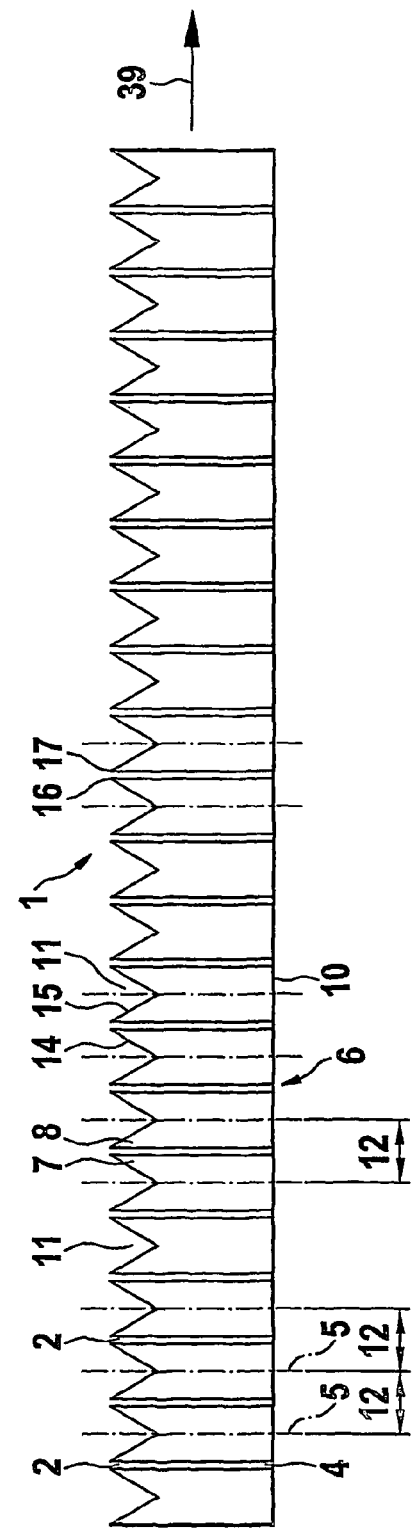
FIG. 3 shows the band-shaped support material with puncturing points punched out on its first face.

FIG. 3 shows the production of recesses which delimit puncturing points on a first face of the band-shaped support material. If necessary, the height h of the test band can at the same time be shortened in this method step. It will be seen from the view in FIG. 3 that recesses 11 are produced on the first face 9 of the band-shaped support material 1. The recesses 11 can, as is shown in FIG. 3, be made triangular, for example. The point of the recesses 11 directed away from the first face 9 preferably coincides with the separating line 5 according to the view in FIG. 2. The recesses 11 are delimited by a first edge 14 and a second edge 15. With reference to the depressions 2 which are produced transversely with respect to the direction of advance 39 in the band-shaped support material 1, the intersection of edges 14, 15 defines a puncturing point 16. This expediently lies in the embossed depression 2, which can be configured as a groove or notch, for example. The puncturing point 16 can further be ground so that it is able to pierce human skin in order to collect a volume of blood. According to the view in FIG. 3, the separating lines 5, along which the individual puncturing/measuring disposable bodies 6 are later separated from the band-shaped support material 1, are provided in a division 12. The division 12 and the spacing of the depressions 2, seen in the direction of advance 39 of the band-shaped support material 1, is dependent on the later width of the individual puncturing/measuring disposable bodies 6 to be produced and can be chosen freely. After the production, shown in FIG. 3, of recesses 11 on the first face 9 of the band-shaped support material 1, a further processing of the band-shaped support material 1 takes place.

It can be seen from the view according to FIG. 4 that the band-shaped support material 1, which is transported in direction of advance 39, is surrounded, in the area of the first face 9, by a soft plastic cover 18, for example of silicone material or any other suitable material. The soft plastic cover 18 can have a U-shaped profile so that the puncturing tips 16 ground and sharpened at the first face 9 of the band-shaped support material 1 are protected from damage in the area of the depressions 2. Moreover, the silicone material cover 18 provides for a permanent sterility of the points 16 at the first face 9 of the band-shaped support material 1. The sterility is produced by irradiation with β or γ radiation or by heat and is maintained by surrounding the band-shaped support material with the soft plastic cover (silicone material cover) 18.

At the second face 10 of the band-shaped support material 1 lying opposite the soft plastic cover 18, a plastic cover 19 is likewise applied. Plastic cover 19 may be made of any suitable plastic material and serves for easier handling of the band-shaped support material 1. Accordingly, harder materials are preferably used. The plastic cover 19 can be used as a grip area 20. The plan view according to FIG. 4 shows the areas of the depressions 2 which extend between the soft plastic cover 18 at the first face 9 and the plastic cover 19 at the second face 10 of the band-shaped support material 1. The separating line 5, along which individual puncturing/measuring disposable bodies 6 are separated from the band-shaped support material 1, is flush with the tip of the recesses 11 which were produced at the first face 9 of the band-shaped support material 1, which define the puncturing points 16 on both sides of the depressions 2 (see view according to FIG. 3).

It will be seen from FIG. 5 that the depressions of the band-shaped support material are provided with a cover and a detection element. In the view according to FIG. 5, the band-shaped support material 1 is provided at the first face 9 with the soft plastic cover 18 for protecting against damage. The plastic cover 19 is arranged lying opposite this at the second face 10 of the band-shaped support material 1. A cover film 21 is applied between the soft plastic cover 18 and the plastic cover 19. At the same time, or separately from this, a detection element 22 narrower than the cover film 21 is applied to the band-shaped support material 1. The detection element 22 is configured in the manner described in German patent application DE 196 29 656 A1, the disclosure of which is expressly incorporated by reference herein, for example, and can be used for the detection of glucose in human blood. The detection element 22 is applied to the band-shaped support material 1 after the latter has been sterilized by β or γ irradiation. Applying the detection element 22 afterwards has the advantage that the radiation-sensitive detection element 22 is not exposed to the sterilizing (β or γ radiation, since such irradiation could greatly impair the functioning or efficacy of the detection element 22. According to the production method proposed according to the invention, the process steps of sterilization and of application of a radiation-sensitive detection element 22 are distinct from one another, so that the detection element 22 is not impaired by the process step of sterilization by β or γ radiation.

As can be seen from the view according to FIG. 5, the areas of the depressions 2 still open in the band-shaped support material I in FIG. 4 are covered both by the cover film 21 and also by the detection element 22 and are no longer visible in the view according to FIG. 5. The depressions extend from the first face 9 to the second face 10 of the band-shaped support material 1 underneath the cover film 21 and underneath the detection element 22.

The view according to FIG. 6 shows an individual puncturing/measuring disposable body 6 with covered puncturing point 16. In the production method proposed according to the invention for combined measuring and puncturing devices for detection of an analyte in liquid, the individual puncturing/measuring disposable bodies 6 are separated from the band-shaped support material 1 along the separating lines 5 shown in FIGS. 2, 3 and 4. These bodies comprise, on both sides of the depression 2, which serves as capillary channel 23, a first lancet part 7 and a second lancet part 8. The separation of the individual puncturing/measuring disposable bodies 6 from the band-shaped support material 1 transported in the direction of advance 39 forms a first separating site 24 on the first lancet part 7 and a second separating site 25 on the second lancet part 8. The depression 2 suitable for capillary liquid transport lies underneath the cover film 21 and underneath the detection element 22. In the lower area of the individual puncturing/measuring disposable body 6, the latter is provided with a portion of the plastic cover 19, which can function as a grip area 20. The first face 9 of the individual puncturing/measuring disposable body 6 shown here is covered by the soft plastic cover 18.

FIG. 7 shows an individual puncturing/measuring disposable body 6 with soft plastic cover 18 removed. The depression 2, which can be formed like a groove or notch in the band-shaped support material 1, ends directly at the puncturing point 16. The puncturing point 16 can have a ground front part similar to an injection needle. A capillary channel mouth 27 of the depression 2 opens out in the puncture point 16. The depression 2, which serves as capillary channel 23 for capillary liquid transport, is formed with a capillary channel length 38. The width of the depression is indicated by reference number 37 and depends on the configuration of the punching or embossing tool with which the depressions 2 are produced in the band-shaped support material 1. The individual puncturing/measuring disposable body 6 comprises a first lancet part 7 and a second lancet part 8, at whose lines of separation 5 from the band-shaped support material 1 a separating side is in each case formed, designated by reference number 24 or 25. The depression 2, which forms the channel 23 suitable for capillary liquid transport, extends continuously from the capillary channel mouth 27 on the first face 9 of the individual puncturing/measuring disposable body 6 to the second face 10 of the band-shaped support material 1, here covered by the plastic cover 19.

Cross sections through the individual puncturing/measuring disposable body 6 are indicated by VIII-VIII and IX-IX and are shown more clearly in FIGS. 8 and 9, respectively.

FIG. 8 shows a cross section, according to the cross section line VIII-VIII in FIG. 7, through a capillary channel designed with a rounded depression base and suitable for liquid transport. The band-shaped support material 1 is covered by the detection element 22 in the cross-sectional plane. The detection element 22 has a thickness 28. The thickness of the band-shaped support material 1, preferably configured as a thin metal film with a thickness of 0.1 to 0.3 mm, is indicated by reference number 30.

In the view according to FIG. 8, the base 4 of the depression 2 is designed with a rounded shape 34. A supply of liquid, for example human blood, is taken up by the capillary channel 23 extending perpendicular to the plane of the drawing in FIG. 8 and suitable for capillary liquid transport. This channel merges into the detection element 22 and forms, in the latter, a saturated zone 33. The supply of liquid 32 that can be taken up in the depression 2 and the capillary channel 23 depends on the depth of the depression 2, i.e. on the depth of embossing into the band-shaped support material 1. With a capillary channel length 38 of approximately 15 mm and a capillary channel width 37 of approximately 0.25 mm, ca. 100 nl of human blood can be taken up in the capillary channel, on condition that the base 4 of the depression 2 has a rounded shape 34. The time needed for a sufficient volume of liquid to pass into the depression 2 functioning as capillary channel 23 and located underneath the cover film 21 and the detection element 22 depends on the configuration of that surface of the band-shaped support material 1 forming the capillary base and on the materials used for cover film 21 and detection element 22. If aluminium, for example, is chosen, its oxidized surface can be made highly hydrophilic.

FIG. 9 shows the formation of a depression of triangular cross section in the band-shaped support material. In this embodiment, the band-shaped support material 1 is covered on its top face by a detection element 22. A supply of liquid 32, for example human blood, passes into the depression 2 designed with a triangular shape 35 and forms a saturated area 33 in the detection element 22. According to the view in FIG. 9, the material thickness of the detection element is identified by reference number 28, while the material thickness of the band-shaped support material 1 is identified by reference number 30.

Depending on the geometry of the depression 2 forming the capillary channel 23, whether its base 4 has a rounded shape 34 or a triangular shape 35, a corresponding supply of liquid can pass by capillary action under the cover film 21 and detection element 22 and wet the detection element portion 22 on the individual puncturing/measuring disposable body 6.

In the method proposed according to the invention, the individual puncturing/measuring disposable body 6 shown in FIGS. 6 and 7 can be separated singly from the band-shaped support material 1; in addition to this, it is also possible, by batchwise perforation, to separate groups of 5 or 10 individual puncturing/measuring disposable bodies 6 from the band-shaped support material 1. If the individual puncturing/measuring disposable bodies 6 are separated in batches or groups, individual perforations can be produced along the virtual separating line 5, said perforations permitting easy separation of the outer-lying individual puncturing/measuring disposable body 6 from the respective batch.

The individual puncturing/measuring disposable body 6 obtained by the production method proposed according to the invention represents a combined puncturing and measuring device whose puncturing point 16 is formed in the band-shaped support material 1 by embossing and whose measuring function is produced in the same production method by applying the detection element 22, with a cover film 21 covering the depressions 2. In the method according to the invention, the band-shaped support material 1 can also be coated with a cover film 21 containing the detection element 22, so that the detection element 22 is situated near the puncturing point 16 formed at one face of the band-shaped support material. In a method variant of this kind, it is possible to dispense with the depressions 2, 23 which are embossed into the band-shaped support material 1 and provide for capillary liquid transport to the detection element 22. If the detection element 22 is applied in the area of the sharpened or ground puncturing point 16, the detection element 22 is wetted directly after insertion of the individual puncturing/measuring disposable body 6 into the human skin. At the time of use of the combined puncturing and measuring device according to the invention, the soft plastic cover 18 surrounding the puncturing points 16 and preferably made of a silicone material is removed manually from the puncturing point 16 without leaving any residues. Removing the soft plastic material cover 18 from the puncturing point 16 without leaving any resides ensures wetting of a detection element 22 applied in the area of the puncturing point 16 or, on the other hand, unimpeded entry of a liquid into the depression 2, 23 which allows capillary liquid transport and can be embossed into the individual puncturing/measuring disposable body 6. Alternatively, instead of the soft plastic material cover 18, a hydrophilic plastic can be selected for covering the puncturing points 16, so that any residues possibly remaining in the area of the puncturing points 16 do not interfere with the wetting behaviour of the sample.

The removal of the soft plastic cover 18, which may be made of silicone material or of a hydrophilic plastic, may also be automated using a measurement system, for example if the measurement system comprises an apparatus with a magazine for receiving the combined puncturing and measuring devices proposed according to the invention for detection of an analyte in liquid. As regards the wetting of the combined puncturing and measuring device, it should be noted that the wetting of the combined puncturing and measuring device takes place in a separate step following the production of a skin incision, by guiding the puncturing point 16 to a drop of blood formed on the skin surface. The puncturing point 16 of the combined puncturing and measuring device can also be guided repeatedly to the drop of blood and inserted repeatedly into the skin incision, in order to achieve contact between the emerging body fluid, for example blood, and the depression 2, 23 forming a capillary channel or the detection element 22 or the combined puncturing and measuring device.

It is now possible to dispense with producing lancets and test strips individually in separate work steps and subsequently joining the individual elements together, so that the method proposed according to the invention is particularly advantageous for industrial scale manufacture and makes production of individual puncturing/measuring disposable bodies 6, representing a combined puncturing and measuring device, very economical and affordable.

Although the invention has been described in detail with reference to illustrated embodiments, variations and modifications exist within the scope and spirit of the invention as described and defined in the following claims.

The invention claimed is:

1. A method for producing combined puncturing and measuring devices for detection of an analyte in liquid, including a support and a detection element, the method comprising the following method steps:
   forming puncturing points on a band-shaped support material,
   sealing the puncturing points by embedding each point in a soft plastic cover such that each surface of the puncturing points is in contact with the soft plastic cover, the soft plastic cover being sized and shaped such that when the cover receives puncturing points therein, the soft plastic cover extends between adjacent puncturing points, and the step of sealing the puncturing points by embedding each point in a soft plastic cover further includes the step of embedding the puncturing points in a continuous soft plastic cover that receives at least two of the puncturing points therein,
   sterilizing the sealed puncturing points and the band-shaped support material such that the embedding of the puncturing points in the soft plastic cover provides for maintaining permanent pre-use sterility of the puncturing points, and
   applying a detection element to the sterilized band-shaped support material.

2. The method according to claim 1, wherein depressions are embossed into the band-shaped support material in order to form a channel suitable for capillary liquid transport.

3. The method according to claim 2, wherein the depressions are embossed transversely with respect to a direction of advance of the band-shaped support material.

4. The method according to claim 2, wherein, on both sides of the depressions, individual puncturing/measuring disposable bodies are separated in sections from the band-shaped support material along virtual separating lines.

5. The method according to claim 4, wherein the virtual separating lines are chosen in accordance with a predeterminable, selectable division.

6. The method according to claim 2, wherein the depressions in the band-shaped support material are designed with a rounding at a base of the depression.

7. The method according to claim 6, wherein the depression base of the depressions is provided with a hydrophilic coating which improves the wetting behavior of a liquid reservoir.

8. The method according to claim 2, wherein the depressions in the band-shaped support material are designed with a depression base which has a triangular contour.

9. The method according to claim 2, wherein a coating covering the depressions and material containing the detection element are applied to the band-shaped support material in one work step.

10. The method according to claim 2, wherein a coating covering the depressions and a material containing the detection element are applied to the band-shaped support material one after the other.

11. The method according to claim 1, wherein the forming step includes the step of forming recesses that define the puncturing points on one face of the band-shaped support material, the recesses being punched out or cut out from the band-shaped support material, with first and second edges being formed.

12. The method according to claim 11, wherein the recesses on the one face of the band-shaped support material are produced so as to be symmetrical with respect to the separating lines.

13. The method according to claim 11, wherein the first and second edges of the recesses defining the puncturing points are ground.

14. The method according to claim 1, wherein a material containing the detection element is applied to the band-shaped support material near the puncturing points.

15. A combined puncturing and measuring device for detection of an analyte in liquid, produced according to claim 1, wherein individual puncturing/measuring disposable bodies have a puncturing point which is provided with a soft plastic cover and comprise a detection element which is applied to the individual puncturing/measuring disposable body after the latter has been sterilized and/or sealed.

16. The method according to claim 15, wherein individual puncturing/measuring disposable bodies are separated singly or in groups from the band-shaped support material transversely with respect to a direction of advance along the separating lines.

17. The method according to claim 16, wherein, in the case of individual puncturing/measuring disposable bodies being separated from the band-shaped support material in groups along the separating lines, perforations are formed to make handling easier.

18. The combined puncturing and measuring device according to claim 15, wherein the detection element is applied to a channel which has been embossed as a depression in the individual puncturing/measuring disposable body and which is suitable for capillary liquid transport.

19. The method according to claim 1, further comprising the step of separating individual puncturing/measuring disposable bodies from the band-shaped support material.

20. The method according to claim 19, wherein the step of applying includes applying a detection element to the band-shaped material having sealed and sterilized puncturing points.

21. The method according to claim 1, further including the step of obtaining a reel of band-shaped support material, wherein the forming step includes recesses being punched out or cut out from the reel of band-shaped support material.

22. The method of claim 1, wherein the soft plastic cover is a piece of homogenous composition.

* * * * *